US008940788B2

(12) United States Patent
Ji et al.

(10) Patent No.: US 8,940,788 B2
(45) Date of Patent: Jan. 27, 2015

(54) ANTI-ANGIOGENIC COMPOSITION CONTAINING MACROLACTIN A AND A DERIVATIVE THEREOF AS ACTIVE INGREDIENTS (71) Applicants: Young-Hoon Ji, Seoul (KR); Dong-Hee Kim, Gimhae-si (KR); Jung-Ae Kim, Daegu (KR); Jae-Seon Kang, Busan (KR); Sung-Uk Chung, Seoul (KR); Sung-Woo Hwang, Busan (KR); Kyung-Ran Kang, Busan (KR); You-Ra Kang, Gyeongsan-si (KR)

(72) Inventors: Young-Hoon Ji, Seoul (KR); Dong-Hee Kim, Gimhae-si (KR); Jung-Ae Kim, Daegu (KR); Jae-Seon Kang, Busan (KR); Sung-Uk Chung, Seoul (KR); Sung-Woo Hwang, Busan (KR); Kyung-Ran Kang, Busan (KR); You-Ra Kang, Gyeongsan-si (KR)

(73) Assignee: Daewoo Pharmaceutical Ind. Co., Ltd., Busan (KR)

( * ) Notice: Subject to any disclaimer, the term of this patent is extended or adjusted under 35 U.S.C. 154(b) by 0 days.

(21) Appl. No.: 13/941,932

(22) Filed: Jul. 15, 2013

(65) Prior Publication Data
US 2013/0303600 A1 Nov. 14, 2013

Related U.S. Application Data (63) Continuation of application No. 13/809,752, filed as application No. PCT/KR2011/001228 on Feb. 23, 2011.

(30) Foreign Application Priority Data

Jul. 16, 2010 (KR) .................... 10-2010-0068886

(51) Int. Cl.
A01N 43/02 (2006.01)
A61K 31/335 (2006.01)
A61K 31/365 (2006.01)

(52) U.S. Cl.
CPC ............. *A61K 31/365* (2013.01); *A61K 31/335* (2013.01)
USPC ....................................... 514/450

(58) Field of Classification Search
None
See application file for complete search history.

(56) References Cited

U.S. PATENT DOCUMENTS

2008/0039407 A1    2/2008    Timmis et al.

OTHER PUBLICATIONS

Gustafson et al. (J. Am. Chem. Soc., 1989, 111, 7519-7524).*
Clinical Trials: Questions and Answers (National Cancer Institute Fact Sheet, May 19, 2006, 1-11).*
Romero-Taberez et al. (Antimicrobial Agents and Chemotherapy, May 2006, 50, 1701-1709).*
Goodman and Gilman (The Pharmacological Basis of Therapeutics, 10th Edition, 2001, McGraw Hill, Chapter 1, pp. 3-29).*
R. K. Jha, et al., Biomedical Compunds from Marine Organisms, Mar. Drugs, vol. 2, pp. 123-146, 2001.
Adamis, et al., "Angiogenesis and Ophthalmic Disease," Angiogenesis, vol. 3, No. 1, pp. 9-14, (1999).
Arbiser, "Angiogenesis and the Skin: A Primer," Journal of the American Academy of Dermatology, vol. 34, No. 3, pp. 486-497 (1996).
Choi, et al., "Characteristics of the squalene synthase inhibitors produced by a Streptomyces species isolated from soils," Canadian Journal of Microbiology, vol. 49, No. 11, pp. 663-668 (2003).
D'Amato, et al., "Angiogenesis inhibition in Age-Related Macular Degeneration," Ophthalmology, vol. 102, No. 9, pp. 1261-1263 (1995).
Fenical, et al., "The Macrolactins a Novel Class of Antiviral and Cytotoxic Macrolides from a Deep-Sea Marine Bacterium," The Journal of the American Chemical Society, vol. 111, No. 19, pp. 7519-7524 (1989).
Folkman, "Angiogenesis in Psoriasis: Therapeutic Implications," Journal of Investigative Dermatology, vol. 59, pp. 40-43 (1972).
Folkman, "Tumor Angiogenesis: Its Possible Role in Metastasis and Invasion," pp. 94-103, Cancer Invasion and Metastasis: Biologic Mechanisms and Therapy, Edited by S.B. Day, et al. (1997).
Folkman, et al., "Relation of Vascular Proliferation to Tumor Growth," International Review of Experimental Pathology, vol. 6, pp. 207-248 (1999).
Hanahan, et al., "Patterns and Emerging Mechanisms of the Angiogenetic Switch during Tumorigenesis," Cell, vol. 86, pp. 353-364 (1996).
Isner, et al., "Angiogenesis and vasculogenesis as therapeutic strategies for postnatal neovascularization," The Journal of Clinical Investigation, vol. 103, No. 9, pp. 1231-1236 (1999).
Koch, "Arthritis & Rheumatism," Journal of the American College of Rheumatology, vol. 41, No. 6, pp. 951-962 (1998).
Koch, "Stimulation of Neovascularization By Human Rheumatiod Synovial Tissue Macrophages," Arthritis & Rheumatism vol. 29, No. 4, pp. 471-479 (1986).
Mollinari, et al., "7-O-Malonyl Macrolactin A, a New Macrolactin Antibiotic from *Bacillus subtillis* Active against Methicillin-Resistant *Staphylococcus aureus*, Vancomycin-Resistant Enterococci, and Small-Colony Variant of *Burkholderia cepacia*," Antimicrobial Agents and Chemotherapy, vol. 50, No. 5, pp. 1701-1709 (2006).
O'Brien, et al., "Neovascular Expression of E-Selectin, Intercellular Adhesion Molecular-1, and Vascular Cell Adhesion Molecule-1 in Human Atherosclerosis and Their Relation to Intimal Leukocyte Content," Circulation, vol. 93, No. 4, pp. 672-682 (1996).
Polverini, "The Pathophysiology of Angiogenesis," Critical Reviews in Oral Biology & Medicine, vol. 6, No. 3, pp. 230-247 (1995).
Stupack, "A role for angiogenesis in rheumatoid arthritis," Brazilian Journal of Medical and Biological Research, vol. 32, pp. 573-581 (1999).
Yoo, et al., "Neuronal Cell Protection Activity of Macrolactin A Produced by *Actinomadura* sp." Journal of Microbiology and Biotechnology. vol. 7, No. 6, pp. 429-434 (1997).

* cited by examiner

*Primary Examiner* — Dennis Heyer
*Assistant Examiner* — Daniel M Podgorski
(74) *Attorney, Agent, or Firm* — Lucas & Mercanti, LLP (57) ABSTRACT

The present invention relates to an anti-angiogenic composition containing macrolactin compounds such as macrolactin A, 7-O-malonyl macrolactin A, and 7-O-succinyl macrolactin A as active ingredients. The macrolactin compounds according to the present invention strongly suppress angiogenesis in in vivo experiments and can be used as a pharmaceutical composition for preventing or treating diseases caused by angiogenesis.

7 Claims, 7 Drawing Sheets

ANTI-ANGIOGENIC COMPOSITION CONTAINING MACROLACTIN A AND A DERIVATIVE THEREOF AS ACTIVE INGREDIENTS

CROSS-REFERENCE TO RELATED APPLICATIONS

This is a Continuation of U.S. patent application Ser. No. 13/809,752 filed Jan. 11, 2013, which is a 371 of PCT/KR2011/001228 filed on Dec. 23, 2011, which claims the priority of KR No. 10-2010-0068886 filed on Jul. 16, 2010, the entire disclosure of each of which are incorporated herein by reference.

TECHNICAL FIELD

The present invention relates to an anti-angiogenic composition containing macrolactin compounds having anti-angiogenic activity, such as macrolactin A (MA), 7-O-malonyl macrolactin A (MMA), and 7-O-succinyl macrolactin A (SMA) as active ingredients. A pharmaceutical composition for preventing or treating diseases caused by angiogenesis is provided by using the anti-angiogenic composition according to the present invention.

BACKGROUND ART

Angiogenesis is a process wherein a new capillary is generated from an existing microvessel. Normal angiogenesis occurs in embryonic development, tissue regeneration and wound treatment, and luteinization—a periodic change in the female reproductive system—and it proceeds under strict control (Folkman J. et al., *Int. Rev. Exp. Pathol.*, 16, pp. 207-248, 1976).

Vascular endothelial cells grow very slowly in adults and are rarely divided compared with other types of cells. The process of angiogenesis progresses with decomposition of the basal membrane of blood vessels by protease due to the stimulation of angiogenesis-stimulating factor, migration and proliferation of vascular endothelial cells, and tubular formation due to differentiation of vascular endothelial cells, which results in reconstruction of blood vessels to form a new capillary.

Several diseases are caused by failure of self-regulation of angiogenesis and abnormal growth of blood vessels. Angiogenesis-related diseases occurring in pathological conditions include angioma, angiofibroma, vascular malformations, cardiovascular diseases such as atherosclerosis, vascular adhesion, scleredema and ophthalmic diseases such as keratoplastic angiogenesis, neovascular glaucoma, diabetic retinopathy, neovascular corneal diseases, spot degenerations, pterygium, retinal degeneration, retrolental fibroplasia and granular conjunctivitis. Chronic inflammatory diseases such as arthritis, skin diseases such as psoriasis, telangiectasis, pyogenic granuloma, seborrheic dermatitis and acne, Alzheimer's and obesity are also related to angiogenesis. Furthermore, growth and metastasis of cancer are necessarily dependent on angiogenesis (D'Amato R. J. et al., *Ophthalmology*, 102(9), pp. 1261-1262, 1995; Arbiser J. L., *J. Am. Acad. Dermatol.*, 34(3), pp. 486-497, 1996; O'Brien K. D. et al. *Circulation*, 93(4), pp. 672-682, 1996; Hanahan D. et al., *Cell*, 86, pp. 353-364, 1996).

Especially in cancer, angiogenesis plays an important role in the growth and metastasis of cancer cells. Tumors are provided with nutrients and oxygen by new blood vessels, which infiltrate the tumors and give cancer cells an opportunity to enter into blood circulation to aid metastasis of cancer (Folkman and Tyler, *Cancer Invasion and Metastasis*, Biological Mechanism and Therapy (S. B. Day, ed.) Raven Press, New York, pp. 94-103, 1977; Polverini P. J., *Crit. Rev. Oral. Biol. Med.* 6(3), pp. 230-247, 1995). A principal reason that chemotherapies or immunotherapies for cancer patients scarcely contribute to increasing the survival rates of patients is metastasis of cancer.

Arthritis, a typical inflammatory disease, is primarily induced by an autoimmune disorder. As the disease progresses, chronic inflammation in synovial bursa between the joints induces angiogenesis and destroys cartilage. That is, synovial cells and vascular endothelial cells proliferate with the aid of inflammation-inducing cytokine, and as angiogenesis progresses, joint pannus, which is connective tissue layer generated in cartilage, is formed to destroy the cushioning cartilage (Koch A. E. et al., *Arthritis. Rheum.*, 29, pp. 471-479, 1986; Stupack D. G. et al., Braz, *J. Med. Biol. Res.*, 32(5), pp. 578-581, 1999; Koch A. E., *Arthritis Rheum.*, 41(6), pp. 951-962, 1998).

Ophthalmic diseases, which make millions of people blind every year, result from angiogenesis (Jeffrey M. I. et al., *J. Clin. Invest.*, 103, pp. 1231-1236, 1999). For example, macular degeneration occurring in the aged, diabetic retinopathy, retinopathy of a precocious child, neovascular glaucoma and neovascular corneal diseases are caused by angiogenesis (Adamis A. P. et al., *Angiogenesis*, 3, pp. 9-14, 1999). Among the diseases, diabetic retinopathy is a complication of diabetes which results in blindness due to the invasion of retinal capillaries into the vitreous body.

Psoriasis, characterized by red spot and scaled skin, is a chronic proliferative disease occurring in skin that is difficult to treat, and involves pain and deformation. While in a normal state keratin cells proliferate once a month, in psoriasis patients they proliferate once a week. For such rapid proliferation, profuse blood must be provided, which forces active angiogenesis (Folkman J., *J. Invest. Dermatol.*, 59, pp. 40-48, 1972).

Anti-angiogenic agents can be applied to treat various angiogenic diseases. Since anti-angiogenic agents are generally administered to patients for a long time, those of low toxicity and which are orally administered are ideal. Thus, there is a great need to develop a novel anti-angiogenic agent with low toxicity.

For a long time, the present inventors have studied macrolide antibiotics having a 24-membered lactone ring, macrolactine derivatives including macrolactin A and their pharmacological mechanisms of action. Macrolactin compounds are produced from unclassified ocean bacteria, *actinomyces* and *Bacillus* strains (Willam Fenical et al., *J. Am. Chem. Soc.*, 111, pp. 7519-7524, 1989; Ik Dong Yoo et al., *J. Microbiol. Biotechnol.*, 7, pp. 429-434, 1997; Gabriella Molinari et al., *Antimicrob. Agents Chemother.*, 50, pp. 1701-1709, 2006), and 23 macrolactin compounds have been identified. Prior studies on the pharmacological activities of the macrolactin compounds are as follows.

MA, isolated for the first time in 1989, suppresses the proliferation of murine melanoma cancer cell and Herpes simplex virus, and protects T-lymphoblast damaged by HIV (Wiliam Fenical et al., *J. Am. Chem. Soc.*, 111, pp. 7519-7524, 1989). Furthermore, it suppresses squalene synthase (Sung Won Choi et al., *Can. J. Microbiol.*, 49, pp. 663-668, 2003), protects brain cells damaged by glutamate (Ik Dong Yoo et al., *J. Microbiol. Biotechnol.*, 7, pp. 429-434, 1997) and has an antibacterial activity against various pathogens including super bacteria (Gabriella Molinari et al., *Antimicrob. Agents Chemother.*, 50, pp. 1701-1709, 2006). In addition, the present inventors confirmed that MA and its derivatives inhibit the formation of inflammatory mediators induced by lipopolysaccharide (LPS) and filed a patent application (PCT/KR2010/003239).

The present inventors confirmed that MA, MMA and SMA were produced from *Bacillus polyfermenticus* KJS-2 (KCCM10769P, hereinafter, "BP2") fermentation or culture medium and identified their structures. Besides the three macrolactin compounds, the present inventors also confirmed by LC/Mass that macrolactin B, macrolactin C, macrolactin D, macrolactin E, macrolactin F, macrolactin G, macrolactin H, macrolactin I, macrolactin J, macrolactin K, macrolactin L, macrolactin M, macrolactin N, isomacrolactinic acid and macrolactinic acid were produced from the BP2 fermentation or culture medium crude extract (Korean Patent No. 10-0895908). However, the present inventors did not confirm the production of macrolactin O, macrolactin P, macrolactin Q, macrolactin R or macrolactin S from BP2.

Macrolactin compounds have various pharmacological activities for their various structures. However, studies about the anti-angiogenesis of macrolactin compounds have never been reported until now. Hence, the present inventors fractionated the crude extract produced from the BP2 fermentation or culture medium including various macrolactin compounds using middle-pressure liquid chromatography (MPLC) and investigated anti-angiogenic activity of each fraction to find that the fractions containing macrolactin compounds suppress angiogenesis, and especially, the fractions containing MA, MMA and SMA strongly suppress angiogenesis. Accordingly, the present inventors highly purified each compound from the MPLC fractions containing the three macrolactin compounds (PCT/KR2010/003239) and investigated the anti-angiogenic activity of each purified macrolactin compound.

CONTENTS OF THE INVENTION

Problems to be Solved

The present inventors confirmed that MA, MMA and SMA strongly suppress angiogenesis, and thus completed the present invention. Accordingly, the object of the present invention is to provide a pharmaceutical composition comprising the macrolactin compounds as active for preventing or treating diseases caused by angiogenesis.

Technical Means

In one aspect, the present invention provides an anti-angiogenic composition comprising at least one of the compounds of Formula 1, Formula 2 and Formula 3 as active ingredients.

In another aspect, the present invention provides a pharmaceutical composition comprising at least one of the compounds of Formula 1, Formula 2 and Formula 3 as active ingredients for preventing or treating angiogenesis-related diseases.

[Formula 1]

$C_{24}H_{34}O_5$
Mol. WT: 402.52
Macrolactin A

[Formula 2]

$C_{28}H_{36}O_8$
Mol. Wt: 488.57
7-O-malonyl macrolactin A

[Formula 3]

$C_{28}H_{38}O_8$
Mol. Wt: 502.6
7-O-succinyl macrolactin A

For the above angiogenesis-related diseases, rheumatoid arthritis, osteoarthritis, septic arthritis, psoriasis, corneal ulcer, age-related macular degeneration, diabetic retinopathy, proliferative vitreoretinopathy, immature retinopathy, ophthalmic inflammation, conical cornea, Sjogren's syndrome, myopia ophthalmic tumor, rejection of corneal transplantation, abnormal cut conglutination, bone disease, proteinuria, disorders of abdominal aneurysm, cartilage loss resulting from traumatic joint damage, neurologic demyelination, cirrhosis, glomerular diseases, immature rupture of embryofetal membrane, inflammatory bowel diseases, periodontal diseases, arteriosclerosis, restenosis, inflammatory diseases of the central nervous system, Alzheimer's disease, skin aging, infiltration and metastasis of cancer, etc. are known.

The present invention is explained in more detail hereinafter.

The macrolactin compounds of the present invention can be obtained by the preparation method disclosed in the patent application (PCT/KR2010/003239) which is owned by the present inventors.

That is, MA, MMA and SMA, which correspond to the compounds of Formula 1, Formula 2 and Formula 3, respectively, are obtained by the processes of fermentation using *Bacillus polyfermenticus* KJS-2 (KCCM10769P) which is isolated by the present inventors, extraction, separation and purification.

The compounds of the present invention obtained from the above method strongly suppressed neovascular formation and metastasis of cancer caused by angiogenesis which were induced by the treatment of angiogenic inducers such as vascular endothelial growth factor (VEGF), tumor necrosis factor-α (TNF-α,) and interleukin-8 (IL-8) in in vivo tests using a chicken chorio-allantoic membrane model; thereby it is confirmed that the compounds can be used as a pharmaceutical composition for preventing and treating angiogenesis-related diseases.

Effect of the Invention

MA, MMA and SMA provided by the present invention strongly suppressed neovascular formation in in vivo tests using a chicken chorio-allantoic membrane model, and therefore the pharmaceutical composition comprising them as active ingredients can be used for preventing and treating diseases caused by angiogenesis.

CONCRETE EXPLANATION TO CARRY OUT THE INVENTION

The present invention provides a pharmaceutical composition comprising MA, MMA or SMA as active ingredients and pharmaceutically acceptable carriers or excipients for preventing or treating diseases caused by angiogenesis.

Herein, the diseases caused by angiogenesis are at least one selected from the group consisting of rheumatoid arthritis, osteoarthritis, septic arthritis, psoriasis, corneal ulcer, age-related macular degeneration, diabetic retinopathy, proliferative vitreoretinopathy, immature retinopathy, ophthalmic inflammation, conical cornea, Sjogren's syndrome, myopia ophthalmic tumor, rejection of corneal transplantation, abnormal cut conglutination, bone disease, proteinuria, disorders of abdominal aneurysm, cartilage loss resulting from traumatic joint damage, neurologic demyelination, cirrhosis, glomerular diseases, immature rupture of embryo-fetal membrane, inflammatory bowel diseases, periodontal diseases, arteriosclerosis, restenosis, inflammatory diseases of the central nervous system, Alzheimer's disease, skin aging, and infiltration and metastasis of cancer.

Hereinafter, the pharmaceutical composition according to the present invention is explained.

The above pharmaceutical composition comprises at least one of MA, MMA and SMA, which are macrolactin compounds produced from the culture medium or fermentation medium of *Bacillus polyfermenticus* strains including BP2, as active ingredients and pharmaceutically acceptable carriers or excipients.

The pharmaceutical composition of the present invention for preventing or treating angiogenesis-related diseases can further include suitable carriers, excipients or diluents conventionally used in manufacturing pharmaceutical compositions.

Examples of the carriers, excipients or diluents which can be included in the pharmaceutical composition of the present invention for preventing or treating angiogenesis-related diseases are lactose, dextrose, sucrose, sorbitol, mannitol, xylitol, erythritol, maltitol, starch, acacia gum, alginate, gelatin, calcium phosphate, potassium silicate, cellulose, methyl cellulose, microcrystalline cellulose, polyvinyl pyrrolidone, water, methyl hydroxyl benzoate, propyl hydroxyl benzoate, talc, magnesium stearate and mineral oil.

The pharmaceutical composition according to the present invention comprising at least one of MA, MMA and SMA can be formulated as oral preparations such as powders, granules, tablets, capsules, suspensions, emulsions, syrups and aerosols, external preparations, suppositories, instillations, eardrops and sterilized injections using conventional preparation methods.

The preparations are formulated by means of conventionally used diluents or excipients such as fillers, extenders, binders, humectants, disintegrating agents and surfactants. Solid preparations for oral administration include tablets, pills, powders, granules, capsules, etc., and they are formulated by mixing at least one excipient such as starch, calcium carbonate, sucrose or lactose and gelatin. In addition to the simple excipients, lubricants such as magnesium stearate and talc are used. Liquid preparations for oral administration are suspensions, gel solutions, emulsions, syrups, etc. In addition to the conventionally used simple diluents such as water and liquid paraffin, various excipients such as humectants, sweetening agents, flavoring agents and preservatives can be included in the liquid preparations. Preparations for parenteral administration include sterilized gel solutions, nonaqueous solutions, suspensions, emulsions, lyophilized preparations, suppositories, instillations and eardrops. For nonaqueous solutions and suspensions, propylene glycol, polyethylene glycol, vegetable oil such as olive oils, injectable esters such as ethyl oleate, etc. can be used. For suppository base, witepsol, macrogol, tween 61, cacao butter, laurinum, glycerogelatin, etc. can be used. For preparing instillations or eardrops, buffering agents such as phosphoric acid, citric acid, tartaric acid, malic acid and succinic acid, and pH adjusters such as hydrochloric acid, sulfuric acid, sodium hydroxide, potassium hydroxide can be also used.

Although the dose of at least one of MA, MMA and SMA vary depending on age, sex or body weight of a patient, a typical dose is in the range of 0.01 to 100 mg/kg per day which can be administered once or in divided unit dosage. The dose of at least one of MA, MMA and SMA may vary depending on administration route, degree of symptoms, sex, body weight, age, etc. Accordingly, the above dose should not limit the scope of the present invention.

The pharmaceutical composition of the present invention can be administered to mammals including rats, mice, cattle, humans, etc. Every administration route may be expected—for example, oral, rectal or intravenous, muscular, subcutaneous, intrauterine or intracerebroventricular injection may be used.

The present invention is explained in more detail by the following examples. However, these examples seek to illustrate the present invention only, and the scope of the present invention is not limited by them.

Materials and Reagents

Fertile eggs were obtained at Baekja Korean native chicken (Cheongsong, Korea). 2-Pyridine carboxaldehyde, 2-acetylfuran and cortisone acetate were obtained at Aldrich Chemical Co. (St. Louis, Mo., USA), VEGF and IL-8 at R&D Systems (Minneapolis, Minn., USA), TNF-α at Invitrogen Life Tech., Whatman filter disc at Whatman (UK), and batimastat at Tocris Bioscience (Ballwin, Mo., USA).

PREPARATION EXAMPLE

Production, Separation and Purification of Samples

MA, MMA and SMA were obtained by the preparation method disclosed in the patent application (PCT/KR2010/003239) owned by the present inventors.

Example 1

CAM Analysis of Suppressive Effect on Angiogenesis

In order to confirm an anti-angiogenic effect of the macrolactin compounds in in vivo test, chorioallantoic membrane (CAM) analysis was carried out (Nguyen M. et al., *Microvascular Res.*, 47, pp. 31-40, 1994). 6±1 fertile eggs were used per group.

Fertile chicken eggs were cultured while maintaining the temperature of 37° C. and the relative humidity of 55%. On the third day of culture, a first small hole was made in the air sac part with a hypodermic needle (Green Cross Medical Corporation, Korea), and a second hole was made in the plat part of the fertile eggs to make a window.

The CAM was separated from the eggshell by expelling the air through the first hole in the air sac, and then the part was cut with a grinding wheel (Multipro 395JA, Dremel, Mexico) to make a window.

A Whatman filter disc #1 (Whatman, USA) was treated with 3 mg/ml of cortisone acetate and dried. The filter disc was treated with 10 μl of VEGF, TNF-α or IL-8 (20 ng/CAM).

Through the pre-made window, the filter disc was put on blood vessel, and then treated with various concentrations of MA, MMA or SMA which was dissolved in DMSO and diluted with PBS.

Three days after treatment, the CAM part with the filter disc was separated and washed with phosphate buffer solution. The photographs were taken by using a stereomicroscope (Leica, Wetzlar, Germany) and Image-Pro Plus software (Media Cybernetics; Silver Spring, Md., USA) to determine the number of bleed vessel branches and to analyze the data.

All data were represented as mean±standard error of mean, and the statistical analysis was done as one-way ANOVA by using GraphPad Prism 4 Software (San Diego, Calif., USA). Multiple comparisons between the differences of each group were made by using the NK (Newman-Keuls) method. When p-value was less than 0.05, the data were regarded as statistically significant.

Figure 1A:
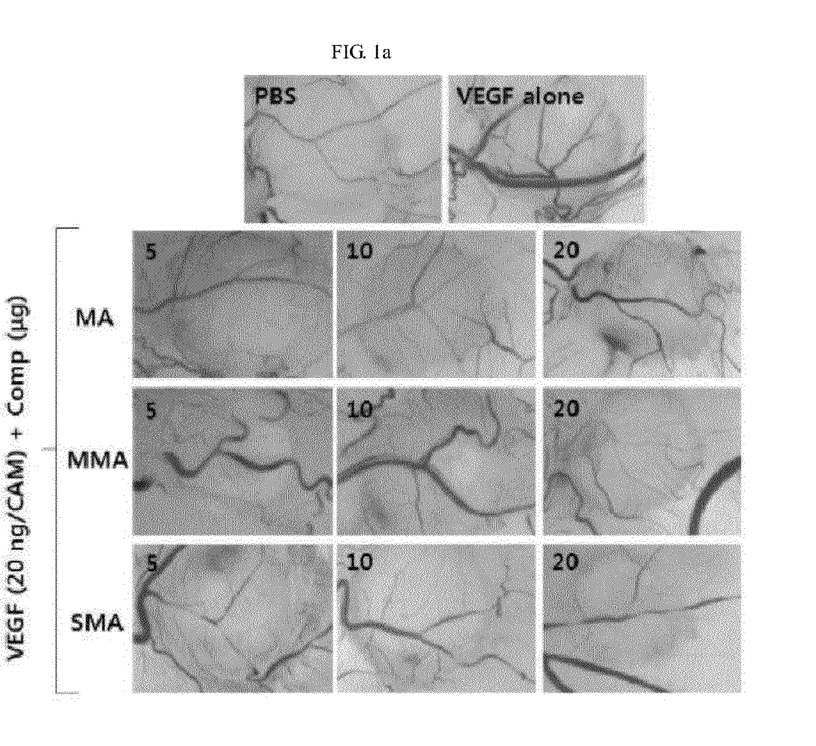
FIG. 1a is composed of photographs of a stereomicroscope for the chorio-allantoic membrane in the Examples showing the suppressive effect of the compounds according to the present invention on neovascular formation induced by VEGF.
Figure 1B:
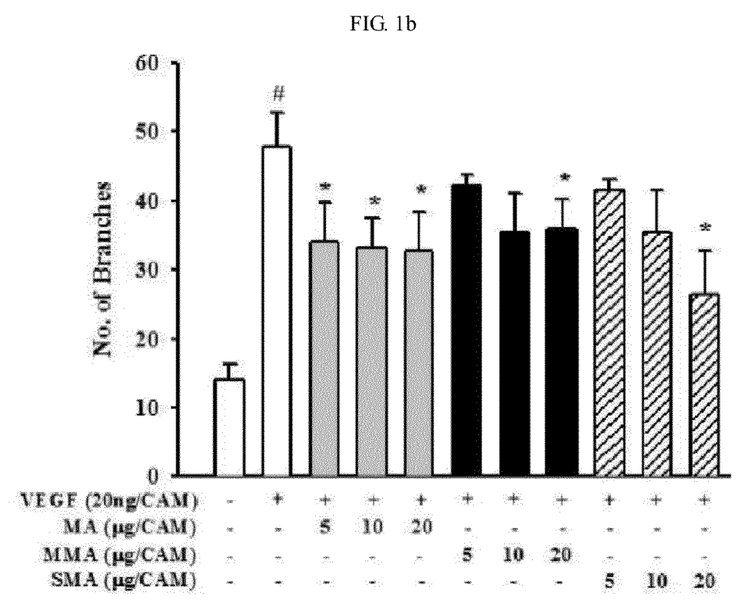
FIG. 1b is a graph showing the suppressive effect of the compounds according to the present invention on neovascular formation induced by VEGF.
Figure 2A:
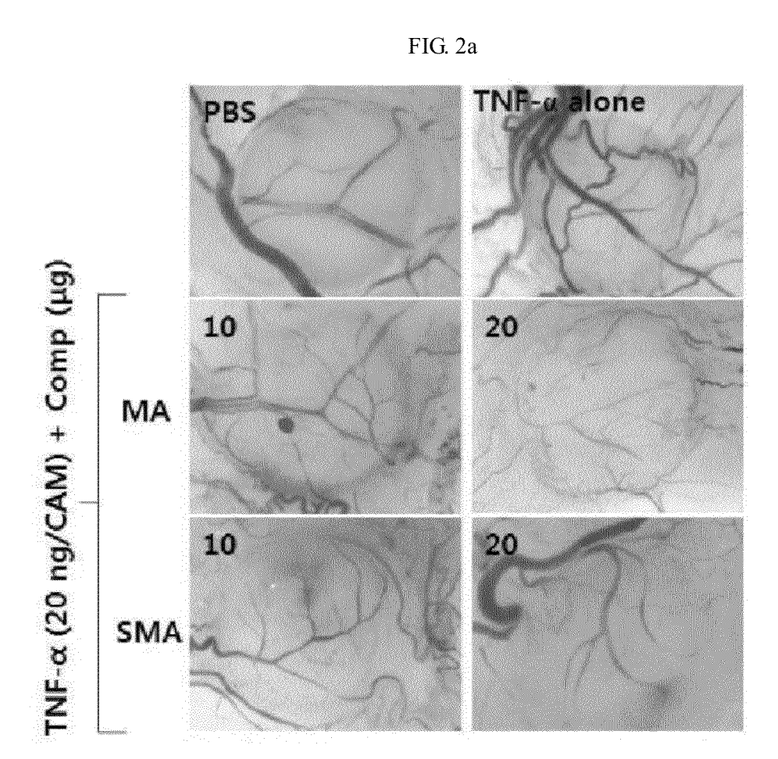
FIG. 2a is composed of photographs of a stereomicroscope for the chorio-allantoic membrane in the Examples showing the suppressive effect of the compounds according to the present invention on neovascular formation induced by TNF-α.
Figure 2B:
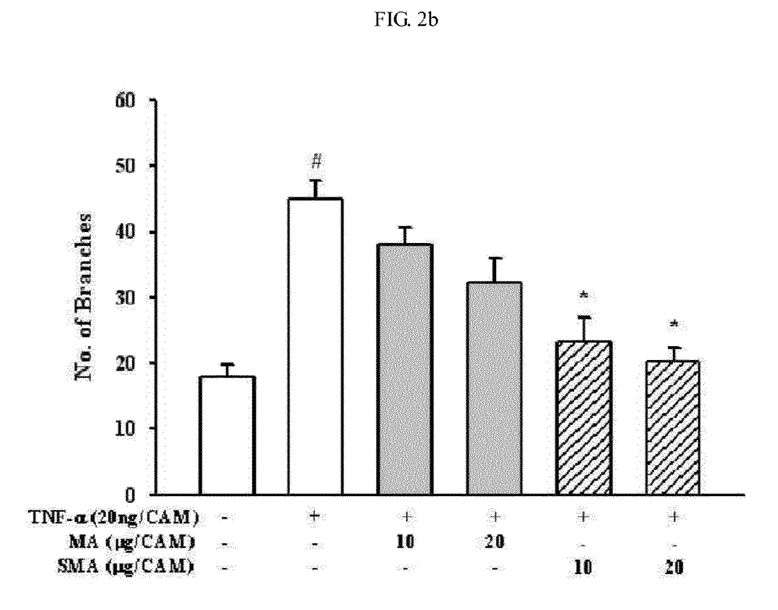
FIG. 2b is a graph showing the suppressive effect of the compounds according to the present invention on neovascular formation induced by TNF-α.
Figure 3A:
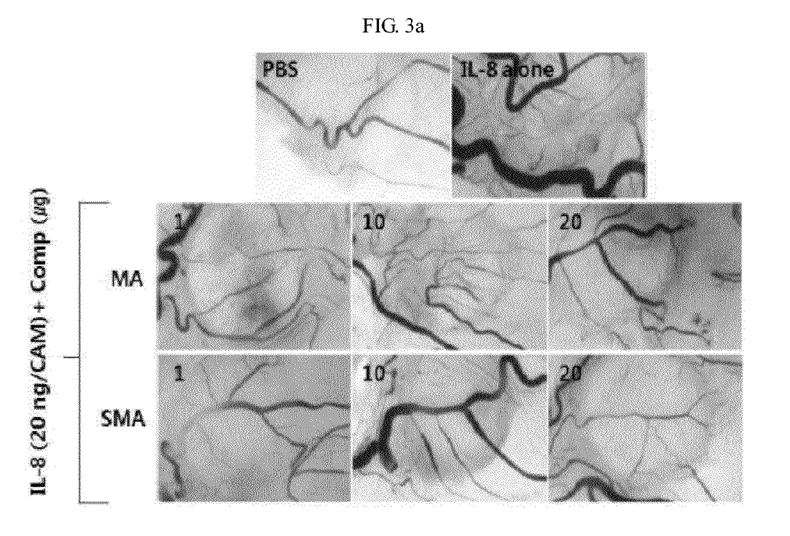
FIG. 3a is composed of photographs of a stereomicroscope for the chorio-allantoic membrane in the Examples showing the suppressive effect of the compounds according to the present invention on neovascular formation induced by IL-8.
Figure 3B:
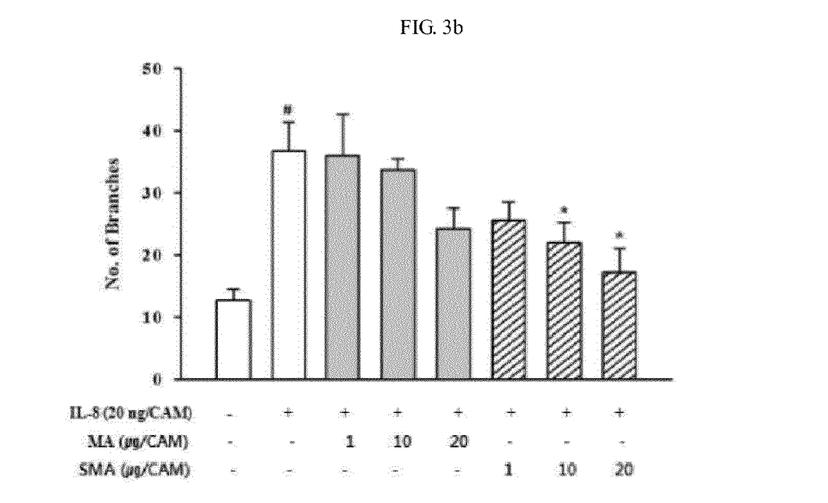
FIG. 3b is a graph showing the suppressive effect of the compounds according to the present invention on neovascular formation induced by IL-8.

The results of the above test are shown in FIGS. 1, 2 and 3.

FIGS. 1, 2 and 3 are photographs of the new blood vessels observed in each group and graphs representing the determined number of blood vessel branches in each group.

As shown in FIGS. 1a and 1b representing the results of each test group treated with PBS, VEGF alone or VEGF and the macrolactin compounds in various concentrations, MA, MMA and SMA strongly suppressed neovascular formation caused by VEGF. Especially, SMA suppressed neovascular formation in a dose-dependent way.

As shown in FIGS. 2a and 2b representing the results of each test group treated with PBS, TNF-α alone or TNF-α and the macrolactin compounds in various concentrations, MA and SMA strongly suppressed neovascular formation caused by TNF-α. Especially, SMA strongly suppressed neovascular formation such that the number of blood vessel branches of the group treated with SMA in 20 μg/CAM was similar to the control group.

As shown in FIGS. 3a and 3b representing the results of each test group treated with PBS, IL-8 alone or IL-8 and the macrolactin compounds in various concentrations, MA and SMA strongly suppressed neovascular formation caused by IL-8. Especially, SMA strongly suppressed neovascular formation such that the number of blood vessel branches of the group treated with SMA in 20 μg/CAM was similar to the control group.

Likewise, neovascular formation caused by angiogenic inducers such as VEGF, TNF-α or IL-8 decreased significantly by treatment of the macrolactin compounds of the present invention.

Example 2

Test of Suppressive Effect on Metastasis of Cancer

Cell Culture

Human fibrosarcoma cells (HT-1080) were cultured in DMEM containing 10% fetal bovine serum (FBS) and 1% penicillin/streptomycin (PS) under the condition of 37° C. and 5% $CO_2$. When the cells grew to fill 80% or more of the culture flask, they were subcultured at a ratio of 1:3 and used in this test.

Test of Suppressive Effect on Metastasis of Cancer

In order to confirm the suppressive effect of the macrolactin compounds on metastasis of cancer in in vitro experiments, an infiltration test of fibrosarcoma cells was carried out by using a 24-well transwell attached with a polycarbonate filter of 8 mm pore size. Firstly, the bottom side of the filter was coated with Collagen Type I (0.5 mg/ml), and then the upper side of the filter was coated with Matrigel (1.5 mg/ml). After coating, the lower part of the insert was filled with a medium containing 5% FBS, and the upper part was filled with serum-free medium human fibrosarcoma cells (HT-1080) which were incubated for 18 hours in a cell incubator. The human fibrosarcoma cells infiltrated into the bottom side of the filter were fixed with methanol and then dyed with hematoxylin and eosin. The infiltrated cells were observed under a microscope, and 3 parts were randomly selected from each filter to take photographs and determine the number of cells (Kim, M. S. et al., *Cancer Res.*, 63, pp. 5454-5461, 2003; Park, B. C. et al., *Eur. J. Pharm.*, 567, pp. 193-197, 2007).

Figure 4A:
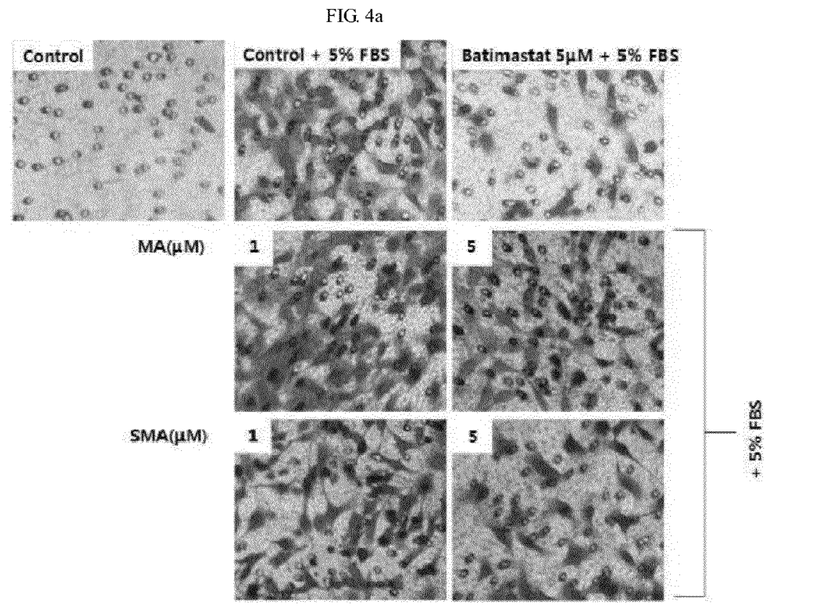
FIG. 4a is composed of photographs showing the suppressive effect of the compounds according to the present invention on metastasis of fibrosarcoma cells induced by 5% FBS.
Figure 4B:
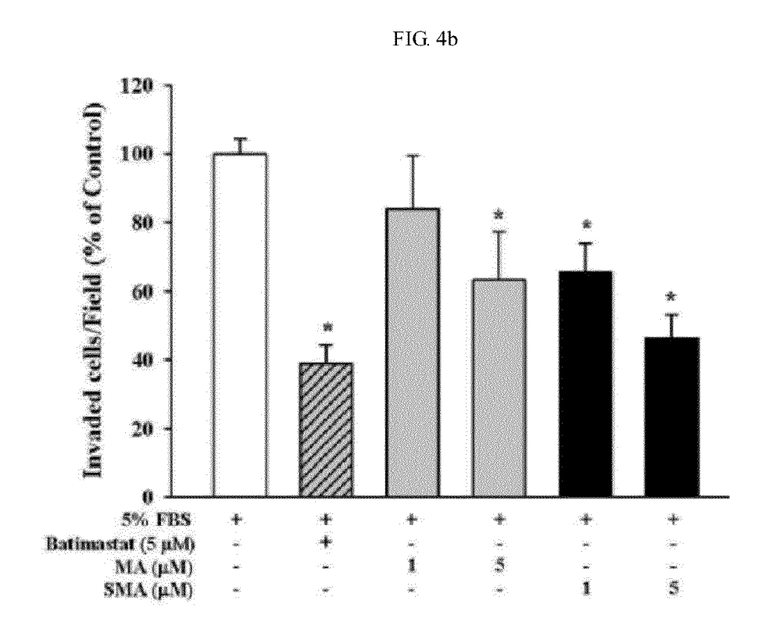
FIG. 4b is a graph showing the suppressive effect of the compounds according to the present invention on metastasis of fibrosarcoma cells induced by 5% FBS.

The above results are shown in FIG. 4.

As shown in FIGS. 4a and 4b, batimastat, an inhibitor of matrix metalloproteinases (hereinafter, MMP), which is essential in metastasis of cancer, was used in a control group for the comparison of the suppressive effect of the macrolactin compounds on metastasis of cancer. The infiltration of fibrosarcoma cells induced by 5% FBS increased, while in the control group treated with MMP inhibitor, batimastat 5 μM, the infiltration was significantly suppressed. MA and SMA suppressed metastasis of fibrosarcoma cells with infiltration induced by 5% FBS in a dose-dependent way. Especially, SMA 1 μM showed significant suppressive effect on the metastasis, and SMA 5 μM showed superior suppressive effect on the metastasis comparable to that of batimastat.

Although the present invention was explained with limited examples and figures, the scope of the present invention should not be limited by them. A skilled artisan could make various revisions and modifications within the technology and ideas of the present invention, and the scope equivalent to the following claims.

We claim:

1. A method of suppressing angiogenesis in fibrosarcoma comprising administering a composition comprising at least one of macrolactin A, 7-O-malonyl macrolactin A and 7-O-succinyl macrolactin A as an active ingredient to a subject in need thereof.

2. The method according to claim 1, wherein the active ingredient is macrolactin A.

3. The method according to claim 1, wherein the active ingredient is 7-O-malonyl macrolactin A.

4. The method according to claim 1, wherein the active ingredient is 7-O-succinyl macrolactin A.

5. The method according to claim 1, wherein the composition comprising at least one of macrolactin A, 7-O-malonyl macrolactin A and 7-O-succinyl macrolactin A is administered at a dosage of 0.01 to 100 mg/kg per day to a subject in need thereof.

6. A method of inhibiting neovascular formation and metastasis of a cancer comprising administering a composition comprising at least one of macrolactin A, 7-O-malonyl macrolactin A and 7-O-succinyl macrolactin A as an active ingredient to a subject in need thereof, wherein the cancer is fibrosarcoma.

7. The method of claim 6, wherein the neovascular formation and metastasis is caused by angiogenesis.

* * * * *